United States Patent [19]

Sumita

[11] Patent Number: 5,444,480
[45] Date of Patent: Aug. 22, 1995

[54] METHOD OF INSPECTING SOLID BODY FOR FOREIGN MATTER

[75] Inventor: Masahiko Sumita, Yokohama, Japan

[73] Assignee: Kirin Techno-System Corporation, Yokohama, Japan

[21] Appl. No.: 139,801

[22] Filed: Oct. 22, 1993

[30] Foreign Application Priority Data

Oct. 26, 1992 [JP] Japan .................. 4-310998

[51] Int. Cl.$^6$ .............................................. H04N 7/18
[52] U.S. Cl. .................. 348/127; 348/128; 348/131; 382/141
[58] Field of Search ............ 348/127, 128, 131; 382/8; 250/223 B; 356/240; H04N 7/18

[56] References Cited

U.S. PATENT DOCUMENTS

| | | | |
|---|---|---|---|
| 3,598,907 | 10/1971 | Drinkuth | 348/127 |
| 4,428,674 | 1/1984 | Giebel | 348/127 |
| 5,305,391 | 4/1994 | Gomibuchi | 348/127 |

FOREIGN PATENT DOCUMENTS

| | | |
|---|---|---|
| 0150846 | 8/1985 | European Pat. Off. . |
| 0491555 | 6/1992 | European Pat. Off. . |
| 1143947 | 6/1989 | Japan . |
| 336948 | 4/1991 | Japan . |
| 336949 | 4/1991 | Japan . |

*Primary Examiner*—Howard W. Britton
*Attorney, Agent, or Firm*—Oblon, Spivak, McClelland, Maier & Neustadt

[57] ABSTRACT

Small pieces of foreign matter on the surface of a cake such as freeze-dried preparations in a vial are detected as distinguished from cake surface irregularities including cake collapses and cracks that should be passed as being acceptable. The cake is imaged by a CCD camera or the like to produce an image signal representing an image of the cake. The level of an image signal which is higher than a predetermined upper limit is set to the upper limit and the level of an image signal which is lower than a predetermined lower limit is set to the lower limit. At least three pixel points, which include a point of interest and surrounding points one on each side of the point of interest, in an inspected region of the image are compared, and the point of interest is judged as being an abnormal point if the point of interest is brighter or darker than the surrounding points. An area in the inspected region is determined as containing foreign matter if the count of abnormal points in the area is larger than a predetermined lower limit and smaller than a predetermined upper limit.

8 Claims, 5 Drawing Sheets

F I G. 4
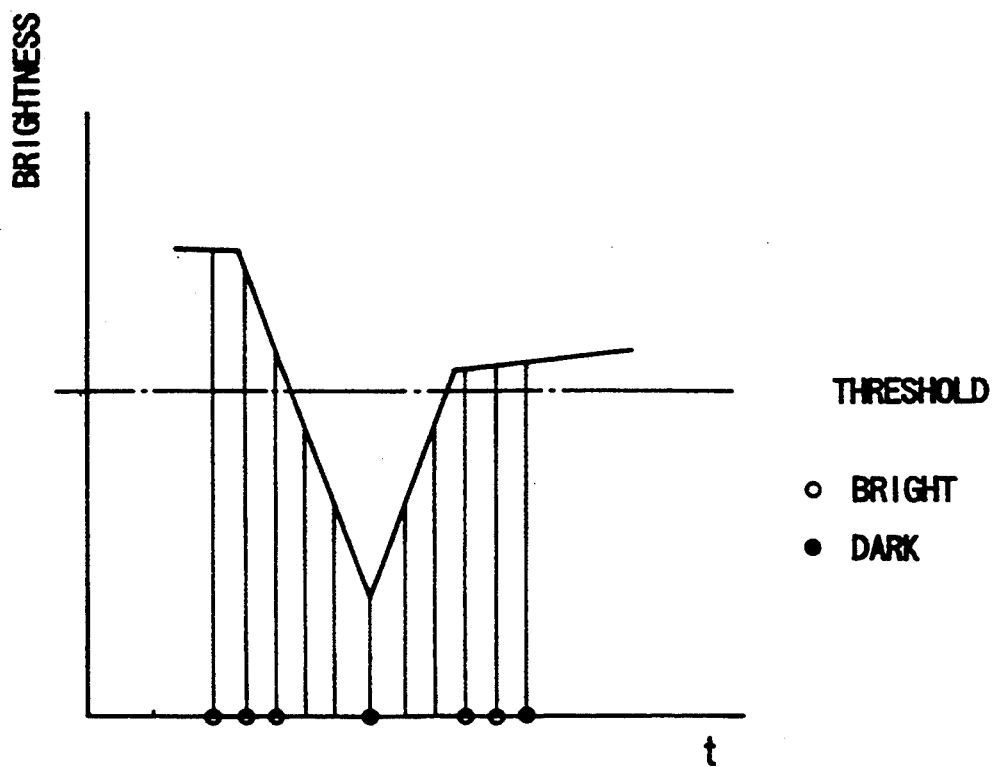

F I G. 5(a)
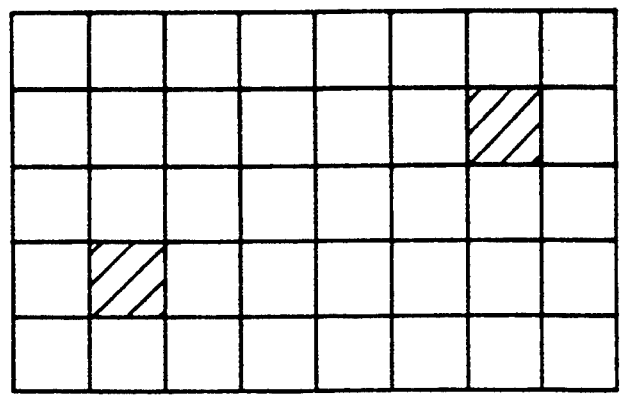
F I G. 5(b)
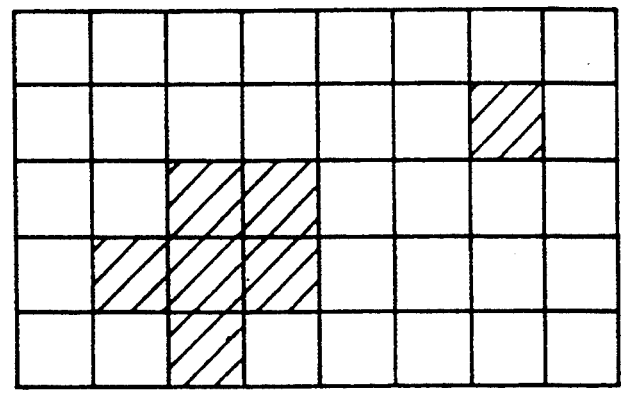
F I G. 5(c)
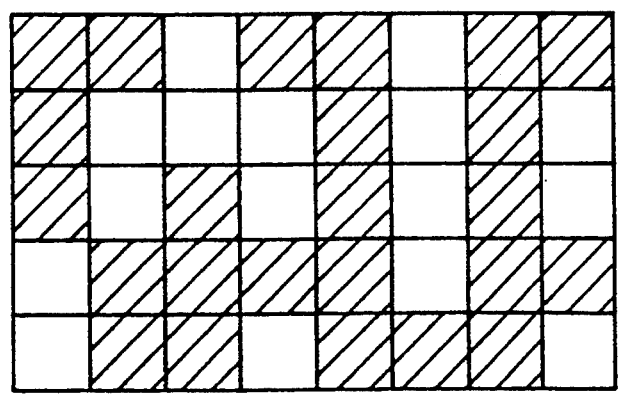

METHOD OF INSPECTING SOLID BODY FOR FOREIGN MATTER

BACKGROUND OF THE INVENTION

1. Field of the Invention

The present invention relates to a method of inspecting a solid body for foreign matter, and more particularly to a method of automatically inspecting a solid body such as freeze-dried preparations filled in a vial for foreign matter thereon based on an image of the vial that is produced by an imaging device.

2. Description of the Related Art

There have heretofore been proposed various automatic inspecting devices for automatically inspecting a solid body (hereinafter referred to as a "cake") such as freeze-dried preparations filled in a small cylindrical container such as a vial or an ampul for foreign matter thereon based on an image of the container.

For example, Japanese laid-open patent publication No. 1-143947 discloses a technique for differentiating between foreign matter on a cake sealed in a vial and powder attached to the vial. According to the disclosed arrangement, the specimen is irradiated with the highly bright and uniform illumination of a balanced mixture of direct light and reflected light to differentiate between foreign matter on the cake and powder attached to the vial.

One approach to the detection of cracks in the lower circumferential region and bottom of a vial and damages of the vial is disclosed in Japanese laid-open utility model publication No. 3-36948. The disclosed device includes a camera and an illuminating system which are positioned in order to image side and bottom surfaces of the vial.

Japanese laid-open utility model publication No. 3-36949 shows a system for detecting damages or cracks in the barrel of a vial and defects, such as a drying failure, dirt, and smear, of the cake sealed in the vial. More specifically, the visual field of an imaging device is divided into two areas to read two images of an inspected region of the vial for higher inspection accracy. Furthermore, diffused light is applied in all directions to the vial to remove any brightness differences on the cake because any convexities on the upper surface of the cake could not be distinguished from foreign matter on the cake if the cake were irradiated with simple uniform light. The publication also discloses the application of a sharply defined light spot to the upper surface of the cake to remove any brightness differences in a cracked region of the cake.

The cake sealed in a vial or the like may sometimes be smeared with a small piece of foreign matter that can barely be recognized by human eyes. Foreign matter on the cake may range from a black spot to a luminous spot on the grayish white surface of the cake. When the cake smeared with foreign matter is imaged, the foreign matter is seen as a small dark or bright area in the screen image. Those cakes which are smeared with detected foreign matter have to be rejected as defects. It has been customary to inspect the cakes sealed in vials for small spots of foreign matter with human eyes. Such an inspecting procedure has been inefficient and time-consuming.

The cake sealed in a vial may also have a peeled surface referred to as a cake collapse or a cracked surface. These surface defects, which also appear as dark or bright areas in the screen image of the cake, should be passed as acceptable because the quality of the cake itself remains unchanged.

One problem is that both small pieces of foreign matter on cakes which have to be rejected as defects and cake collapses or cracked cake surfaces which have to be passed as acceptable are seen as dark or bright areas in the screen image. Cake collapses or cracks are usually large enough to be easily recognized by human vision, whereas small pieces of foreign matter on cakes are much smaller than those cake surface irregularities. Therefore, dark or bright areas representing small pieces of foreign matter in the screen image are less distinct than dark or bright areas representing cake surface irregularities such as cake collapses or cracks, and cannot easily be recognized.

The prior arrangements disclosed in the above publications do not offer effective solutions. Specifically, it is difficult to distinguish between small pieces of foreign matter and cake surface irregularities with highly bright and uniform illumination. When illuminating light is applied to the vial to remove any brightness differences that are caused on the cake by cake collapses or cracks, any brightness differences that are caused by small pieces of foreign matter on the cake are also removed, and these small pieces of foreign matter cannot be seen in the screen image. If the illuminating light is adjusted in intensity to detect small pieces of foreign matter in the screen image, then cake collapses or cracks are also detected as bright or dark areas and cannot be distinguished from the small pieces of foreign matter.

SUMMARY OF THE INVENTION

It is therefore an object of the present invention to provide a method of inspecting a solid body for foreign matter to differentiate between small pieces on the solid body and surface irregularities of the solid body for rejecting a solid body smeared with small pieces of foreign matter as a defect and passing a solid body with surface irregularities as acceptable.

According to the present invention, there is provided a method of inspecting a solid body for foreign matter thereon, comprising the steps of (a) producing an image signal representing an image of a solid body, (b) setting the level of an image signal which is higher than a predetermined upper limit to the upper limit and the level of an image signal which is lower than a predetermined lower limit to the lower limit, (c) comparing at least three pixel points, which include a point of interest and surrounding points one on each side of the point of interest, in an inspected region of the image, and judging the point of interest as being an abnormal point if the point of interest is brighter or darker than the surrounding points, and (d) determining an area in the inspected region as containing foreign matter if the count of abnormal points in the area is greater than a predetermined lower limit and smaller than a predetermined upper limit.

In the step (b), the level of an image signal which is higher than a predetermined upper limit is set to the upper limit and the level of an image signal which is lower than a predetermined lower limit is set to the lower limit. Therefore, an image signal of a bright area which has a level higher than the upper limit or a dark area which has a level lower than the lower limit, which image signal may be produced from a collapse or a crack on a surface of the solid body, is clamped to the upper or lower limit level. The upper and lower limits are selected such that the levels of image signals indicative of small pieces of foreign matter fall in a band range between the upper and lower levels. Accordingly, bright and dark areas produced by surface collapses or cracks are excluded, so that image signals produced by small pieces of foreign matter can be detected with ease.

In the step (c), at least three pixel points, which include a point of interest and surrounding points one on each side of the point of interest, in an inspected region of the image are compared, and the point of interest is judged as being an abnormal point if the point of interest is brighter or darker than the surrounding points. Therefore, if the size of a small piece of foreign matter is smaller than the distance between the surrounding points and the small piece of foreign matter is positioned between the surrounding points, then the point of interest at the small piece of foreign matter is judged as an abnormal point. Thus, a bright or dark spot produced by a small piece of foreign matter can be detected as an abnormal point from within a bright or dark area in the image which is produced by a surface irregularity such as a surface collapse or crack.

In the step (d), if the count of abnormal points in the area is larger than an upper limit, then the area is not determined as being defective. A cluster of abnormal points due to a surface irregularity, which have not been detected in the above steps (b), (c) is much greater than a cluster of abnormal points due to small pieces of foreign matter. Therefore, if clustered abnormal points whose count is larger than the upper limit are not judged as defective, such a surface irregularity can be passed as acceptable. However, small pieces of foreign matter that are to be removed are detected as abnormal points, and can reliably be determined as defective.

The above and other objects, features, and advantages of the present invention will become apparent from the following description when taken in conjunction with the accompanying drawings which illustrate a preferred embodiment of the present invention by way of example.

BRIEF DESCRIPTION OF THE DRAWINGS

FIG. 4 is a diagram illustrative of a three-point comparison step; and

FIGS. 5(a) through 5(c) are diagrams illustrative of an area calculation step.

DETAILED DESCRIPTION OF THE PREFERRED EMBODIMENT

An automatic inspecting device for automatically inspecting a vial has an imaging unit such as a CCD camera or the like for imaging a vial and a cake sealed therein at various angles. The automatic inspecting device detects a defective vial through calculations effected on the image that is produced by the imaging unit, and automatically rejects the detected defective vial from a conveyor line. There are a wide variety of items or defects to be checked with respect to a vial and a cake sealed therein, including a damage of the vial, a crack of the vial, foreign matter on the case among others. In the following description, the automatic inspecting device inspects a cake sealed in a vial for small pieces of foreign matter on the cake.

Figure 1:
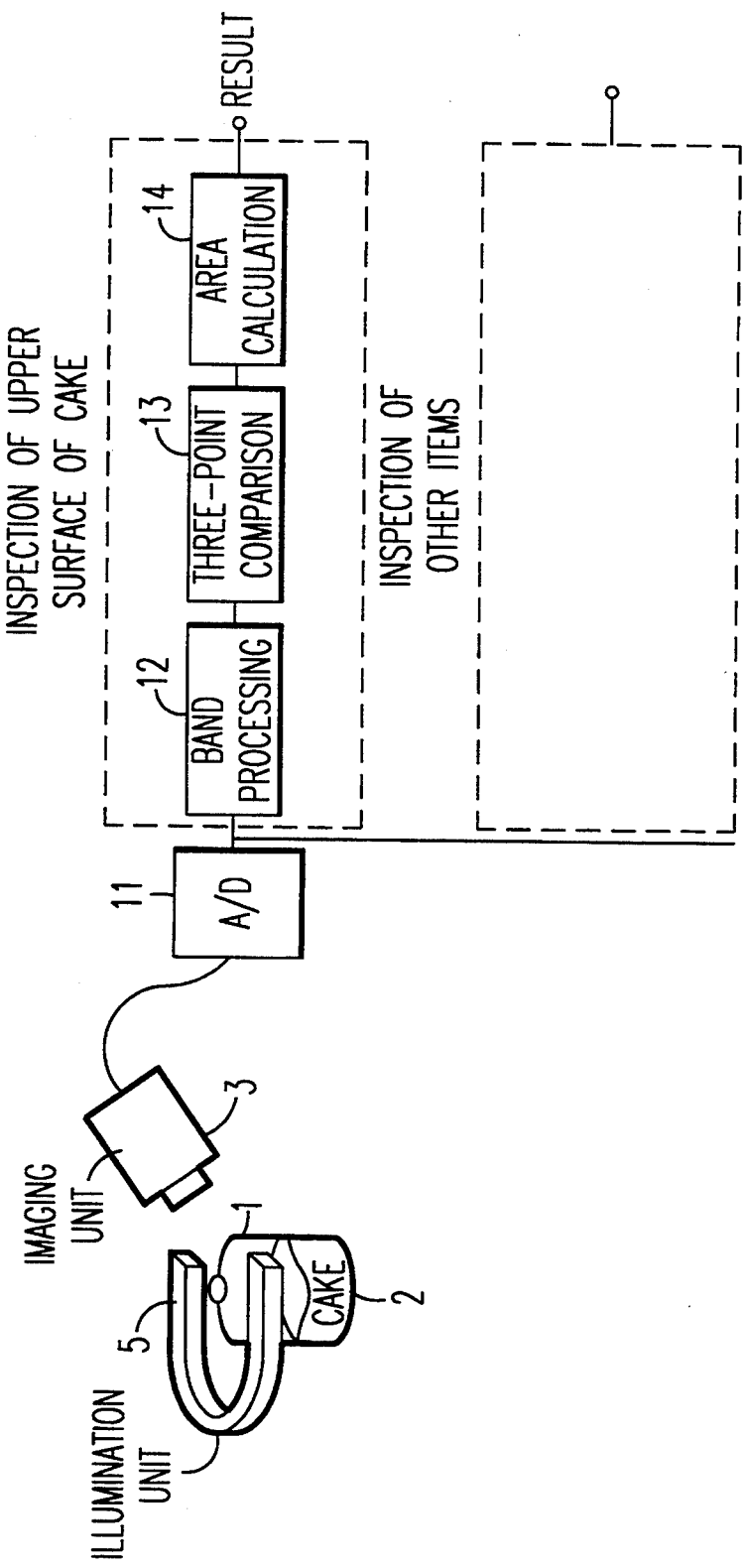
FIG. 1 is a schematic view, partly in block form, of an automatic inspecting device for automatically inspecting a vial based on a method according to the present invention.

As shown in FIG. 1, a vial 1 with a cake 2 sealed therein is fed by a conveyor line to a predetermined imaging position in front of an imaging unit 3 such as a CCD camera and an illuminating unit 5. In the imaging position, the upper surface of the cake 2 is irradiated with a uniform light emitted by the illuminating unit 5. At this time, while the vial 1 is rotated about its vertical axis, the imaging unit 3 produces image signals of the entire upper surfaces of the cake 2.

The imaging unit 3 supplies a image signal representing the image of an upper surface of the cake 2 to an A/D converter 11, which converts the analog image signal to an 8-bit digital image signal (having 256 steps of gradation). The automatic inspecting device subsequently processes the digital image signal through digital data calculations.

Any small pieces of foreign matter on the upper surface of the cake 2, which can barely be recognized by human eyes, have to be distinguished from cake surface irregularities including cake collapses and cracks which may be included in the image. Such a distinguishing process is composed of a band processing step 12, a three-point comparison step 13, and an area calculation step 14.

Figure 2:
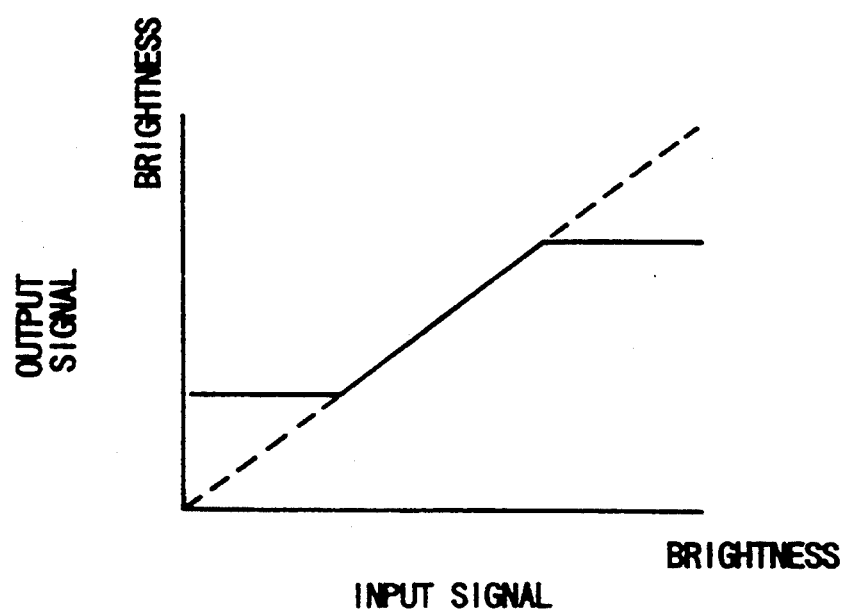
FIG. 2 is a diagram illustrative of a band processing step.

The band processing step 12 sets image signals whose brightness is higher than a predetermined upper limit level to the upper limit level, and also set image signals whose brightness is lower than a predetermined lower limit level to the lower limit level. FIG. 2 illustrates the band processing step 12. As can be understood from FIG. 2, an input image signal whose brightness is higher than a predetermined upper limit level representing a slightly bright area, e.g., an input signal representing a luminous area, is converted into an output image signal with the upper limit level, and an input image signal whose brightness is lower than a predetermined lower limit level representing a slightly dark area, e.g., an input signal representing a dark area, is converted into an output image signal with the lower limit level.

The intensity of the light emitted by the illuminating unit 5 and the upper and lower limit levels are selected such that a image signal representing a small piece of foreign matter that is to be detected falls in a brightness range between the upper and lower limit levels. According to the band processing step 12, a image signal representing a luminous area such as a cake collapse which should be passed as acceptable and a image signal representing a dark area such as a cake crack which should also be passed as acceptable are converted to image signals having slightly bright and dark levels, respectively. Consequently, any image signals representing cake surface irregularities of high contrast are removed, allowing image signals representing small pieces of foreign matter to be detected easily.

Figure 3A:
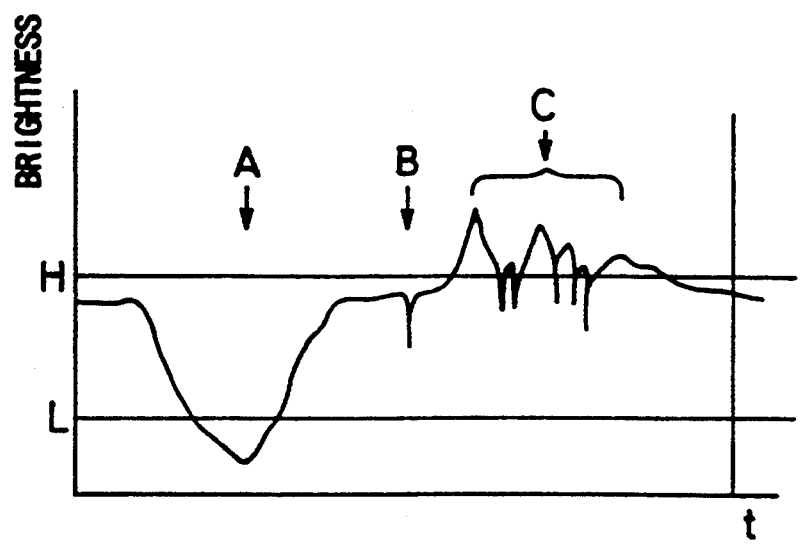
FIG. 3(a) is a diagram of a image signal before it is band-processed.
Figure 3B:
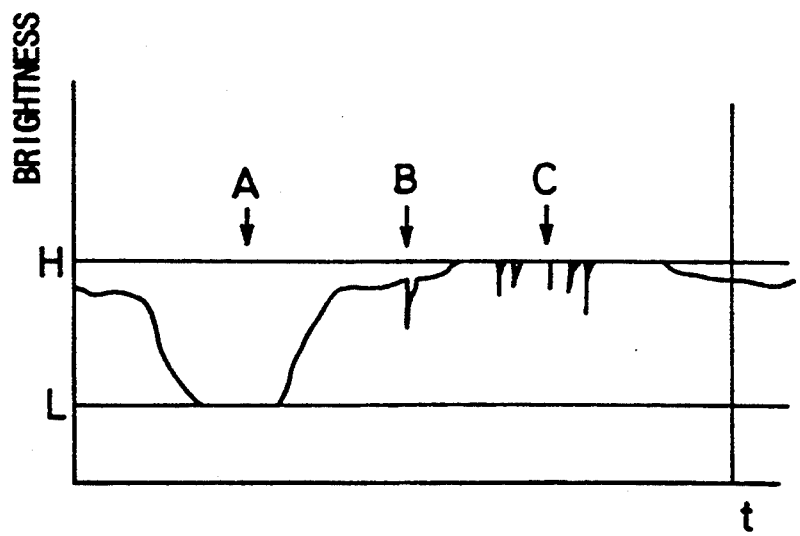
FIG. 3(b) is a diagram of a image signal after it is band-processed.

The upper surface of the cake 2 is more or less curved, and hence its brightness is not uniform. Upper and lower levels H, L are established in order to be able to detect bright and dark areas caused by small pieces of foreign matter. Each pixel of the image in an inspected region is scanned, and its image signal is band-processed into a image signal with the upper and lower limit levels H, L. More specifically, FIG. 3(a) shows a image signal before it is band-processed, and FIG. 3(b) shows a image signal after it is band-processed. In FIG. 3(a), the image signal before it is band-processed contains a dark area A shown as a wider valley and representing a cake crack which is to be accepted, a dark area B shown as a narrower valley and representing a small piece of foreign matter which is to be rejected, and a bright area C representing a cake collapse which is to be accepted. In FIG. 3(b), the band-processed image signal has the dark area A removed below the lower limit level L, and the bright area C removed above the upper limit level H. As shown in FIG. 3(b), highly contrast bright levels which were contained in the bright area C are removed though minute valleys caused by minute powdery cake surface peel-off remain in the image signal. Accordingly, the dark area B can easily be recognized and detected by subsequent calculations.

The three-point comparison step 13 compares the brightness levels of at least three points positioned closely to each other within the inspected region of the image, determines whether the brightness of a point of interest, which is one of the three points that is positioned between the other two points which are referred to as surrounding points, is higher or lower than the brightness of the surrounding points or not, and judges the point of interest as an abnormal point if the brightness of the point of interest is higher or lower than the brightness of the surrounding points. If the size of a small piece of foreign matter at the point of interest is smaller than the distance between the surrounding points and the small piece of foreign matter is positioned between the surrounding points, then when the small piece of foreign matter is luminous, the point of interest is bright and the surrounding points are dark, with the result the point of interest is judged as an abnormal point, and when the small piece of foreign matter is dark, the point of interest is dark and the surrounding points are bright as they are on the upper surface of the cake, with the result the point of interest is also judged as an abnormal point.

A cake surface crack at the point of interest often has its dimension larger than the distance between the surrounding points, and hence the point of interest is frequently not judged as an abnormal point. A cake surface crack having a width as large as a small piece of foreign matter may be judged as an abnormal point. Since a crack is produced linearly, a large number of linear abnormal points are produced in a certain area. A cake collapse at the point of interest also often has its dimension larger than the distance between the surrounding points, and hence the point of interest is frequently not judged as an abnormal point. A powdery cake collapse having a dimension as large as a small piece of foreign matter is judged as an abnormal point by the above three-point comparison step. In this case, a number of abnormal points are produced in a certain area because of a powdery cake collapse.

By suitably selecting the distance between the surrounding points depending on the dimension of foreign matter to be rejected as a defect, such foreign matter that is to be rejected can reliably be detected as a cluster of abnormal points.

The three-point comparison step 13 is composed of the step of converting at least three pixel points including a point of interest and surrounding points one on each side of the point of interest to binary signals each representing a bright or dark level with a constant threshold, and the step of logically processing the binary signals to judge the point of interest as an abnormal point if one of the surrounding points, the point of interest, and the other surrounding point represent either bright, dark, and bright levels, respectively, or dark, bright, and dark levels, respectively.

FIG. 4 is illustrative of the three-point comparison step 13. The image is horizontally or vertically scanned, and each of the pixels of the image is compared with a threshold and converted into a binary signal which represents a bright level if its value is greater than the threshold and a dark level if its value is smaller than the threshold. Then, the binary signal at a certain point (pixel) of interest and the binary signals at two surrounding points (pixels) that are spaced from each other a certain number of pixels are processed in a logic operation. If one of the surrounding points, the point of interest, and the other surrounding point represent either bright, dark, and bright levels, respectively, or dark, bright, and dark levels, respectively, then the point of interest is judged as an abnormal point. As shown in FIG. 4, there may be employed three surrounding points on each side of a point of interest, and the point of interest may be judged as an abnormal point if one of the surrounding points on each side of the point of interest satisfies the above logic relationship. The level of the threshold, the distance between the point of interest and the surrounding points, and the number of surrounding points may be set to suitable values depending on the condition of the cake 2, the size of foreign matter on the cake 2, and other factors. As described above, the three-point comparison step is carried out by converting a pixel into a binary signal with a threshold and logically processing the binary signal. Since any point of interest can be checked by only comparison and logic operation, it is not necessary to calculate the numerical difference between bright and dark pixels. Consequently, the circuit arrangement for executing the three-point comparison step is much simpler than the circuit arrangement that is designed to calculate the numerical difference between bright and dark pixels, and the three-point comparison step itself is much faster than the calculation of the numerical difference between bright and dark pixels.

The area calculation step 14 counts abnormal points within a certain area in the inspected region, and determines the area as containing foreign matter if the count is greater than a certain lower limit and smaller than a certain upper limit. Cake collapses and cracks which are of a relatively large size are not judged as an abnormal point by the above three-point comparison step. However, small cake collapses and cracks which are comparable in size with small pieces of foreign matter tend to give rise to a cluster of abnormal points. If a cluster of abnormal points larger in number than a certain level within a certain area is not judged as defective, then clustered abnormal points that are caused by small cake collapses and cracks, which have not been decided as acceptable by the three-point comparison step, may be passed as acceptable by the area calculation step 14.

It is possible to cause small pieces of foreign matter that are to be removed to appear as a cluster of abnormal points by selecting suitable settings such as the distance between surrounding points in the three-point comparison step. In the area calculation step, abnormal points whose count ranges between the lower and upper limits can be judged as representing foreign matter. The lower limit is effective to exclude occasional abnormal points produced by electric noise or the like.

It has empirically been known that occasional abnormal points should not be interpreted as abnormal points.

FIGS. 5(a) through 5(c) illustrate the area calculation step. In the area calculation step, pixels in a certain area in the inspected region of the image are successively scanned, and abnormal points in the area are counted. In the illustrated examples, an area in which pixels are to be counted is composed of 8×5=40 pixels, and the upper limit of abnormal points is 20 and the lower point of abnormal points is 3. In the examples shown in FIGS. 5(a) and 5(c), the areas are judged as not containing foreign matter. In the example shown in FIG. 5(b), the area is judged as containing foreign matter. The abnormal points in the area shown in FIG. 5(a) are interpreted as being caused by occasional electric noise, and the abnormal points in the area shown in FIG. 5(c) are interpreted as being caused by cake collapses. The examples shown in FIGS. 5(a) and 5(c) should be passed as being acceptable. The abnormal points in the area shown in FIG. 5(c) are interpreted as being caused by small pieces of foreign matter. The example shown in FIG. 5(b) should be rejected as being defective. Successive areas in inspected region of the image are scanned, and the above area calculation step is carried out with respect to the successive areas.

When the cake 2 is judged as being smeared with foreign matter as shown in FIG. 5(b), a signal is applied to the conveyor line to remove the corresponding vial 1 as being defective. As described above, the automatic inspecting device processes the image of the cake 2 according to the above steps 12, 13, 14 to detect small pieces of foreign matter on the cake 2 as distinguished from cake surface irregularities including cake collapses and cracks that should be accepted. Therefore, the process of inspecting cakes in vials for small pieces of foreign matter thereon, which cannot easily be carried out by human eyes, can automatically be effected according to the present invention.

While the detection of foreign matter on the cake sealed in a vial has been described by way of example, the principles of the present invention are also applicable to a wide range of inspection processes for inspecting solid bodies in transparent containers for foreign matter thereon.

Although a certain preferred embodiment of the present invention has been shown and described in detail, it should be understood that various changes and modifications may be made therein without departing from the scope of the appended claims.

What is claimed is:

1. A method of inspecting a solid body for foreign matter thereon, comprising the steps of:
    (a) producing an image signal representing an image of a solid body;
    (b) setting a level of an image signal which is higher than a predetermined upper limit to an upper limit and another level of an image signal which is lower than a predetermined lower limit to a lower limit; and
    (c) comparing at least three pixel points, which include a point of interest and surrounding points one on each side of the point of interest, in an inspected region of the image, and judging said point of interest as being an abnormal point if the point of interest is brighter or darker than said surrounding points.

2. A method as claimed in claim 1, and further comprising:
    (d) determining an area in said inspected region as containing foreign matter if a count of abnormal points in said area is larger than a predetermined lower limit and smaller than a predetermined upper limit.

3. A method according to claim 1, wherein said step (c) comprises the steps of:
    converting each of said pixel points to a binary signal each representing a bright or dark level with a constant threshold; and
    logically processing the binary signals of the pixel points to judge said abnormal point existing on said solid body.

4. A method according to claim 1, wherein said image signal is a digital image signal converted from an analog signal of an imaging unit.

5. A method according to claim 1, wherein said solid body is a cake of a freeze-dried preparation filled in a vial.

6. A method according to claim 1, wherein a distance between said surrounding points is larger than a size of a small piece of foreign matter.

7. A method according to claim 1, wherein said level of predetermined upper limit is lower than the level of an bright area produced from a collapse on a surface of said solid body.

8. A method according to claim 1, wherein said level of predetermined lower limit is higher than the level of a dark area produced from a crack on a surface of said solid body.

* * * * *